US006309677B1

(12) United States Patent
Gorenbein et al.

(10) Patent No.: US 6,309,677 B1
(45) Date of Patent: *Oct. 30, 2001

(54) MULTI-CAROTENOID PRODUCT

(75) Inventors: David Gorenbein, Costa Mesa; Idrees A. Siddiqui, Fullerton; Ernie R. Ceja, La Mirada, all of CA (US); Christine M. Horvath, Portland, MI (US)

(73) Assignee: Amway Corporation, Ada, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/047,106

(22) Filed: Mar. 24, 1998

(51) Int. Cl.[7] .................................................. A61K 33/00
(52) U.S. Cl. ...................... 424/764; 424/439; 514/725; 514/783; 514/763; 514/766; 585/351
(58) Field of Search .................................. 424/764, 439; 514/725, 783, 763, 766; 585/351

(56) References Cited

U.S. PATENT DOCUMENTS

| | | | |
|---|---|---|---|
| 3,039,877 | 6/1962 | Borenstein | 99/81 |
| 3,492,202 | 1/1970 | Bohinski | 195/28 |
| 4,199,895 | 4/1980 | Avron et al. | 47/1.4 |
| 4,439,629 | 3/1984 | Rüegg | 585/803 |
| 4,680,314 | 7/1987 | Nonomura | 514/725 |
| 4,713,398 | 12/1987 | Nonomura | 514/725 |
| 4,851,339 | 7/1989 | Hills | 435/67 |
| 4,981,699 | * 1/1991 | Inada et al. | 426/7 |
| 5,019,668 | 5/1991 | Keat et al. | 585/864 |
| 5,206,025 | 4/1993 | Courteille et al. | 424/439 |
| 5,310,554 | 5/1994 | Haigh | 424/439 |
| 5,382,714 | 1/1995 | Khachik | 568/834 |
| 5,455,280 | 10/1995 | Baranowitz | 514/763 |
| 5,648,564 | 7/1997 | Ausich et al. | 568/834 |

FOREIGN PATENT DOCUMENTS

| | | |
|---|---|---|
| 0 242 148 | 10/1987 | (EP) . |
| 9619217 | * 6/1996 | (WO) . |
| 9747278 | * 12/1997 | (WO) . |

OTHER PUBLICATIONS

Mangels A, Holden J, Beecher G, Forman M, Lanza E. Carotenoid content of fruits and vegetables: An evaluation of analytic data. *J Am Diet Assoc* 1993;93:284–96.

Lachance P. Dietary intake of carotenes and the carotene gap. *Clin Nutr* 1988;7:118–22.

White W, Stacewicz–Sapuntzakis M, Erdman Jr J, Bowen P. Pharmacokinetics of b–carotene and canthaxanthin after ingestion of individual and combined doses by human subjects. *Journal of the American College of Nutrition* 1994;13:665–71.

Ziegler R, Colavito E, Hartge P, McAdams M, Schoenberg J, Mason T, Fraumeni Jr J.Importance of α–carotene, beta–carotene, and other phytochemicals in the etiology of lung cancer. *JNCI* 1996;88:612–15.

Hussein L, El–Tohamy M. Vitamin A potency of carrot and spinach carotenes in human metabolic studies. *International Journal of Vitamin and Nutritional Research* 1990;60:229–35.

Jacques P, Halpner A, Blumberg J. Influence of combined antioxidant nutrient intakes on their plasma concentrations in an elderly population. *Am J Clin Nutr* 1995;62:1228–33.

Tsushima M, Maoka T, Katsuyama M, Kozuka M, Matsuno T, Tokuda H, Nishino H, Iwashima A. Inhibitory effect of natural carotenoids on Epstein–Barr virus activation activity of a tumor promoter in Raji cells. A Screening study for anti–tumor promoters. *Biol Pharm Bull* 1995;18:227–33.

Kostic D, White W, Olson J. Intestinal absorption, serum clearance, and interactions between lutein and b–carotene when administered to human adults in separate or combined oral doses. *Am J Clin Nutr* 1995;62:604–10.

van den Berg H, van Schaik F, van Vliet T. b–carotene absorption and cleavage in men: Interactions with lycopene and lutein. Presented at the 11th International Symposium on Carotenoids, Leiden, Netherlands, Aug. 1996.

* cited by examiner

*Primary Examiner*—Dwayne C. Jones
*Assistant Examiner*—C. Delacroix-Muirheid
(74) *Attorney, Agent, or Firm*—Brinks Hofer Gilson & Lione

(57) ABSTRACT

A composition is provided that includes carotenoid extracts derived from a plurality of natural sources. Carotenoids are extracted from natural sources such as palm fruit, algae and marigold flowers and combined in a single product. The product may include carriers such as yellow bees wax, soybean oil and lecithin and may be in a form suitable for oral ingestion.

9 Claims, No Drawings

MULTI-CAROTENOID PRODUCT

BACKGROUND OF THE INVENTION

Carotenoids are a family of chemical compounds that occur naturally in plants and animals. Non-exhaustive examples of carotenoids are beta-carotene, alpha-carotene, gamma-carotene, lycopene, zeaxanthin, capsanthin and lutein. Each natural source of carotenoids has a distinct array of different carotenoids. For example, it is known that algae contains a mixture of alpha, beta and gamma carotene.

Carotenoids have significant health benefits. For example, beta-carotene is a pre-cursor to Vitamin A, a vital nutrient for human beings and it has been suggested that beta-carotene inhibits heart disease and cancer. Consequently, many people wish to maximize their carotenoid intake. Fruits and vegetables are a desired source of carotenoids because of their nutritional value, cost and availability. Unfortunately, the amount of carotenoids present in natural sources is so small that an inordinate amount of fruits and vegetables would have to be digested to obtain a desired amount of carotenoids.

Thus, methods have been devised to extract and concentrate beta-carotene from various sources. U.S. Pat. No. 5,310,554 to Haigh describes a method for making high-purity natural beta-carotene by extracting algae with organic solvents and chromatographing the extract on a column of alumina. U.S. Pat. No. 4,680,314 to Nonomura describes a method for purifying beta-carotene by extracting algae with an edible oil.

In addition, several manufacturers have attempted to synthetically manufacture beta-carotene. For example, Hoffmann La Roche, a Swiss pharmaceutical and chemical company, manufactures synthetic all-trans-beta-carotene. Synthetic carotenoid compounds, however, almost exclusively contain a specific conformation of a particular carotenoid and contain only trace amounts of other carotenoids or other conformations of the particular carotenoid.

These carotenoid products are either derived synthetically or derived from a single source and fail to provide a balanced supply of carotenoids. Because these products contain a very narrow range of carotenoids, the benefits are commensurately narrow. Each carotenoid, and individual isomers and conformations thereof, possesses unique and distinctive characteristics and benefits. Not all of the benefits associated with each carotenoid are known or understood. Moreover, the exact amount and type of carotenoids present in the individual sources is not always known. As a result, the known carotenoid products are not able to provide each of the benefits, known and unknown, associated with the many different carotenoids.

Consequently, there is a need for a carotenoid product that is able to provide a comprehensive regimen consisting of a wide variety of different carotenoids.

SUMMARY OF THE INVENTION

In order to provide a comprehensive, effective carotenoid regimen, despite this lack of knowledge of the presence or effect of each carotenoid in a particular natural source, a multi-carotenoid product is provided that includes a plurality of carotenoids, derived from a plurality of sources, in a single product or unit dosage form. Preferably, extracts of palm fruit, algae and marigold flowers are used. Most preferably, these extracts are combined with soybean oil, yellow wax and lecithin in a form suitable for oral ingestion. Surprisingly, the carotenoid product of the present invention is a highly effective and beneficial means to supplement carotenoid intake.

A method of making a multi-carotenoid product is provided where at least one source of alpha-carotene and beta-carotene is combined with at least one source of gamma-carotene, lycopene or lutein.

DESCRIPTION OF THE PREFERRED EMBODIMENT

The multi-carotenoid products of the present invention comprise carotenoid extracts derived from a plurality of sources. In a preferred embodiment there are at least three sources. Preferably, each source is a natural source. The natural carotenoid extracts of the present invention may be derived from any natural source that contains carotenoids. Natural sources are those sources that are organic in composition, such as living things, and are not the result of artificial chemical synthesis. The preferred sources are plants. Non-limiting examples of such sources are marigold flowers, palm fruit, algae (preferably of the class Chlorophyta, more preferably of the genera Dunaliella or Chlorococcus), spinach, broccoli, alfalfa, tomatoes and carrots. Most preferred are palm fruit, Dunaliella algae and marigold flowers.

While it is preferred to use only natural sources of carotenoids, specific carotenoids, or specific conformations of carotenoids, may be supplemented through the use of artificial or synthetic carotenoid products. Synthetic carotenoid products generally consist of a very narrow range of carotenoids and essentially comprise a single conformation of a specific carotenoid. Consequently, the use of synthetic carotenoids is not a desirable means of providing a wide variety of carotenoids; however, the use of synthetic carotenoids is an effective means of providing a very specific amount of a particular carotenoid.

The carotenoids of the present invention may be isolated from their sources by any means available. Preferably, the carotenoids are isolated through solvent extraction. More preferably, the carotenoid extract is further purified through chromatography and/or removal of the extracting solvent. In a most preferred embodiment the carotenoids are extracted with a natural, edible oil to the exclusion of toxic volatile organic compounds. An example of such a process is provided in U.S. Pat. No. 4,680,314 to Nonomura, which is incorporated herein by reference in its entirety. In the preferred embodiment carotenoids are derived from at least the following sources: (1) extracted from Dunaliella algae with a vegetable oil solvent as described in U.S. Pat. No. 4,680,314, and available from Nutrilite Products, Inc. under the trade name PROVATENE (2) extracted from palm fruit oil as described in European Patent Application No. 0 242 148 (which is incorporated herein by reference in its entirety) and manufactured by Quest International under the trade name CAROPLEX and (3) extracted from marigold flowers as described in U.S. Pat. Nos. 5,382,714 and 5,648,564 (which are incorporated herein by reference in their entirety) and available from Kemin. In a most preferred embodiment, the carotenoids are derived only from Dunaliella algae, palm fruit and marigold flowers.

Following is an example of how carotenoids may be extracted from palm oil. A column was filled with 2.5 liters of spherical silica gel having a particle distribution of 50 to 600 $\mu$m according to the dry process, and subsequently, 150 g of acetone was fed into this column. Further, the column was washed with 15 liters of hexane, and it was confirmed that the acetone concentration in the effluent from the column bottom became 1000 ppm.

A crude palm oil containing 600 ppm of carotene (all calculated on trans-$\beta$-carotene, as hereinafter) was converted to a methyl ester with methanol, and further subjected to extracting concentration with methanol/water solvent mixture to obtain a carotene-containing concentrate containing 15% of carotene.

The carotene-containing concentration (75 g) was diluted with 1425 g of hexane containing 1000 ppm of acetone and fed into the above column. Subsequently, elution was conducted with the use of hexane containing 1000 ppm of acetone, and the fractions from the point when the red portion began to flow out from the column bottom to completion were collected. The amount of the eluant fed in this operation was 2.5 cm/min based on a vacant column.

When the solvent was evaporated under reduced pressure from the collected red solution, 14 g of purified carotene with a carotene concentration of 72% was obtained. The carotene concentration degree was found to be 4.8-fold, and the carotene recovery 89.6%.

In addition, the multi-carotenoid product of the present invention may include a number of different carriers and/or binders to provide the multi-carotenoid product in a consumable form. e.g., by oral ingestion. The useful and suitable carriers and binders are known to those of skill in the art and are typically neutral, non-toxic additives that facilitate consumption and absorption of the product by the user. Examples of liquid carriers are vegetable oils, such as corn and soybean oil, and mineral oil. Examples of solid carriers and binders are yellow bees wax, glucose, sucrose, starch, lactose, mannitol, magnesium stearate, magnesium carbonate, talcum, and cellulose. Preferably, these ingredients are derived from natural sources. In the preferred embodiment the carrier is a combination of soybean oil, yellow bees wax and lecithin.

It is preferred to provide the multi-carotenoid product with the carriers and binders described above as a unit dosage in a softgel capsule. Suitable softgel capsules are available from R.P. Scherer, St. Petersburg, Fla.

The relative amounts of the carotenoids and the carrier depends upon the desired carotenoid dose to be administered. Consequently, the carotenoids can comprise from about 0.01 % to about 99.99% by weight of the multi-carotenoid product. Preferably, the carotenoids comprise from about 0.1 % to about 25%, more preferably from about 1 % to about 5%.

Similarly, the relative amounts of the individual carotenoid sources is highly variable. The amount of each particular carotenoid source in the multi-carotenoid product depends on which particular carotenoid is most desired and upon the concentration of the carotenoids in the sources.

The most preferred embodiment of the present invention is detailed in Table 1.

TABLE 1

| INGREDIENT | WEIGHT % |
| --- | --- |
| Soybean Oil | 49.71 |
| Yellow Bees Wax | 11.03 |
| Algal Extract | 29.41 |
| Lecithin | 4.90 |
| Palm Fruit Extract | 3.43 |
| Marigold Flower Extract | 1.52 |

The algal extract comprises about 2.15% beta-carotene and about 0.23% alpha-carotene in a corn oil suspension. The palm fruit extract comprises about 10% alpha-carotene, about 19% beta-carotene, about 0.36% gamma-carotene, and about 0.03% lycopene in vegetable oil. The marigold flower extract comprises about 20% lutein in corn oil suspension and is available from Kemin. The product is packaged in a soft-gel caplet provided by R. P. Scherer. Included in the composition is soybean oil, yellow bees wax and lecithin. These components act as a carrier for the carotenoid extracts and create an easily ingestible product.

In addition to the above compositions, a method of making comprehensive carotenoid compositions is also highly useful. Sources of carotenoids are selectively chosen to complement one another and create a product having a wide range of carotenoids. For example, a source that has a particularly high concentration of one carotenoid, but lacking in a second carotenoid, would be combined with a source that has a particularly high concentration of the second carotenoid. In a preferred embodiment, at least one source of alpha-carotene and beta-carotene is combined with at least one source of gamma-carotene, lycopene or lutein. It is preferred that the total amount of carotenoids is at least about 2% by weight.

Of course, it should be understood that a wide range of changes and modifications can be made to the embodiments described above. It is intended, therefore, that the foregoing description illustrates rather than limits this invention, and that it is the following claims, including all equivalents, that define this invention.

What is claimed is:

1. A multi-carotenoid composition derived from a plurality of sources comprising:

a. an algal extract, the algal extract comprising about 0.1% to about 3% beta carotene and about 0.1% to about 2.0% alpha carotene;

b. a palm fruit extract, the palm fruit extract comprising about 0.5% to about 30% alpha carotene and about 0.5% to about 60% beta carotene; and c. a marigold flower extract, the marigold flower extract comprising about 0.1% to about 97% lutein;

wherein the composition contains a comprehensive regimen of carotenoids that is not obtainable from any single source of carotenoids.

2. The composition of claim 1 wherein the algal extract is extracted from algae of the class Chlorophyta.

3. The composition of claim 1 wherein the algal extract is extracted from algae of the genera Dunaliella or Chlorococcus.

4. The composition of claim 1 wherein the algal extract further comprises an edible oil.

5. The composition of claim 1 wherein the palm fruit extract further comprises an edible oil.

6. The composition of claim 1 wherein:

a. the algal extract is extracted from Dunaliella algae with an edible oil; and b. the palm fruit extract is extracted from palm fruit with an organic solvent, chromatographed on a silica or alumina column and resuspended in an edible oil.

7. The composition of claim 1 comprising:

a. from about 5 to about 35% of the algal extract;

b. from about 1 to about 10% of the palm fruit extract; and c. from about 1 to about 5% of the marigold extract.

8. The composition of claim 1 further comprising:

a. soybean oil;

b. yellow bees wax; and c. lecithin.

9. The composition of claim 8 comprising:

a. from about 30 to about 60% soybean oil;

b. from about 5 to about 20% yellow bees wax;

c. from about 0 to about 10% lecithin;

d. from about 5 to about 35% of the algal extract;

e. from about 1 to about 10% of the palm fruit extract; and f. from about 1 to about 5% of the marigold extract.

* * * * *